United States Patent
Kienzle et al.

(10) Patent No.: US 6,288,280 B1
(45) Date of Patent: Sep. 11, 2001

(54) RACEMIZATION OF ATROPISOMERIC BIS (PHOSPHINE OXIDE) COMPOUNDS

(75) Inventors: Frank Kienzle, Flüh; Michel Lalonde, Basel; Rudolf Schmid, Basel; Shaoning Wang, Basel, all of (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/594,643

(22) Filed: Jun. 15, 2000

(30) Foreign Application Priority Data

Jul. 9, 1999 (EP) .................................................. 99113306

(51) Int. Cl.$^7$ ..................................................... C07F 9/53
(52) U.S. Cl. ............................................. 568/14; 549/218
(58) Field of Search ............................... 568/14; 558/404; 564/15; 549/218

(56) References Cited

U.S. PATENT DOCUMENTS

| | | |
|---|---|---|
| 5,274,125 | 12/1993 | Broger et al. . |
| 5,334,766 * | 8/1994 | Cereghetti et al. ..................... 568/14 |
| 5,430,191 | 7/1995 | Foricher et al. . |
| 5,872,273 * | 2/1999 | Saito et al. .............................. 556/21 |
| 6,162,929 * | 12/2000 | Foricher et al. .......................... 549/6 |

OTHER PUBLICATIONS

Helvetica Chimica Acta, 74, p 370 (1991).

* cited by examiner

Primary Examiner—Jean F. Vollano

(74) Attorney, Agent, or Firm—George W. Johnston; William H. Epstein; John P. Parise

(57) ABSTRACT

A process for the racemization of atropisomeric bis (phosphine oxide) compounds of formula I:

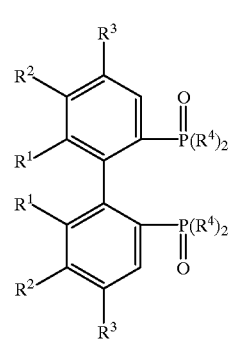

I in their (S) or (R) or non-racemic form, is useful for preparing optical active bisphosphine ligands, that form optical active complexes with transition metals. Racemization is thermal and carried out in high or low boiling solvent, under normal or elevated pressure at $10^5$ to $3.5 \times 10^7$ Pa. Heating is performed in a system that allows heating up to 400° C. (reactor, autoclave, aluminum block, round-bottom flask with heating/stirring mantle and the like) or by microwave irradiation or in the melt at a temperature from 260 to 400° C.

16 Claims, No Drawings

RACEMIZATION OF ATROPISOMERIC BIS (PHOSPHINE OXIDE) COMPOUNDS

SUMMARY OF THE INVENTION

The subject invention provides a process for the racemization of a compound of the formula:

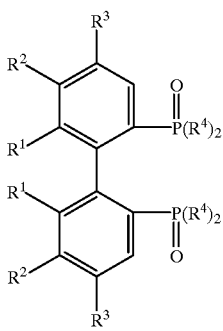

I which is present in the (R) form, the (S) form, or a non-racemic mixture of the (R) form and (S) form. In the compound of formula I, $R^1$ is $C_{1-8}$-alkoxy and $R^2$ is hydrogen, $C_{1-8}$-alkyl, or $C_{1-8}$-alkoxy. Alternatively, $R^1$ and $R^2$ taken together are methylenedioxy or ethylenedioxy. $R^3$ is hydrogen, $C_{1-8}$-alkyl, or $C_{1-8}$-alkoxy. $R^4$ is phenyl or phenyl monosubstituted in the meta- or para-position by $C_{1-8}$-alkyl, $C_{1-8}$-alkoxy, di- $C_{1-8}$-alkylamino, trialkylsilyl or phenyl. This process comprises heating the compound of formula I to a temperature of from about 260° C. to about 400° C. for a time sufficient to cause racemization of the compound of formula I.

DETAILED DESCRIPTION OF THE PREFERRED EMBODIMENTS

The subject invention will now be described in terms of its preferred embodiments. These embodiments are set forth to aid in understanding the invention but are not limiting.

The present invention is concerned with a novel process for the racemization of atropisomeric compounds of formula I,

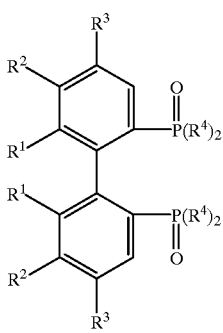

I

The optical active compounds of formula I above are known, as are the intermediates for the preparation of optically active bisphosphine ligands of formula II,

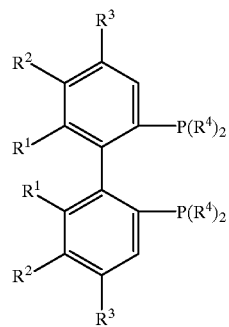

II which form optically active complexes with transition metals. These complexes are used as catalysts in a number of asymmetric reactions.

Synthesis of optically active intermediates of formula I and ligands of formula II by known processes typically use a racemic mixture (mixture of equal amounts of both enantiomers) of the product, that is resolved for the preparation of the optical active ligands of formula II, which are in turn used for the preparation of catalysts. The synthesis of optically active bisphosphine ligands of formula II thus involves the formation of a racemic mixture of the bis (phosphine oxide) of formula I, subsequent racemic resolution and reduction to obtain the desired enantiomer or reduction to the racemic bisphosphine of formula II followed by racemic resolution. The present invention provides a method to use the undesired enantiomer of the intermediate of formula I in order to improve the efficiency of the synthesis of optical active ligands of formula II.

The present invention is thus concerned with a novel process for the racemization of atropisomeric compounds of formula I,

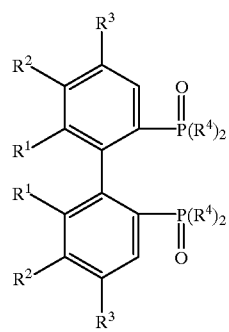

I which are present in the (R) or (S) form or a non-racemic mixture of the (R) and (S) form and wherein $R^1$ signifies $C_{1-8}$-alkoxy and $R^2$ signifies hydrogen, $C_{1-8}$-alkyl, $C_{1-8}$-alkoxy or $R^1$ and $R^2$ together signify methylenedioxy or ethylenedioxy $R^3$ signifies hydrogen, $C_{1-8}$-alkyl or $C_{1-8}$-alkoxy and $R^4$ signifies phenyl or substituted phenyl, characterized in that the racemization is thermal and carried out at a temperature from 260 to 400° C., preferably from 280 to 380° C.

The term "racemization" signifies the transition of an optical active compound towards the corresponding racemate. A racemate signifies a mixture of equal amounts of both enantiomers. It is to be understood that racemization need not be complete to be within the scope of the invention. Thus, the transformation of a (R) to (S) mixture that is in the ratio of 10 to 1 via the subject process into a more racemic mixture of 6 to 4 would be considered within the scope of the invention.

The term "atropisomeric" indicates the stereochemistry of compounds in which the free rotation along a bond is hindered and optical activity results. Atropisomerism is a special case of axial chirality.

The term "$C_{1-8}$-alkyl" signifies in the scope of the present invention hydrocarbons with 1 to 8 carbon atoms, i.e. straight-chain or branched alkyl groups such as, for example, methyl, ethyl, propyl, isopropyl, butyl, isobutyl, tert.-butyl, pentyl, isopentyl, neopentyl, hexyl, isohexyl, tert.-hexyl, heptyl, and octyl.

The term "$C_{1-8}$-alkoxy" signifies a $C_{1-8}$-alkyl group as defined above which is bonded via an oxygen atom. Methoxy, ethoxy, propoxy, isopropoxy, butoxy, and the like can be mentioned as example.

The term "substituted phenyl" signifies in the scope of the present invention phenyl groups which are monosubstituted in the meta- or para-position, preferably in the para-position. Suitable substituents for the phenyl group are $C_{1-8}$-alkyl, preferably methyl; or $C_{1-8}$-alkoxy, preferably methoxy; or di-$C_{1-8}$-alkylamino, preferably dimetylamino; or trialkylsilyl, preferably trimethylsilyl; or substituted by a phenyl group.

According to the invention, the racemization of the compounds of the formula I is carried out by heating the compound in a solvent or in the melt at a temperature from 260 to 400° C. The "melt" means a liquid resulting from the heating of a compound of formula I. The heating is carried out in a device which allows for heating up to 400° C. For small scale the heating can be carried out e.g. with a heating/stirring mantel, an aluminum heating block, an electrically heated reactor or autoclave and the like or by microwave irradiation. For larger scale the heating can be carried out e.g. in reactors or autoclaves. The reaction is carried out batchwise or in a continuous manner.

In a preferred way, the racemization of the compounds of the formula I is carried out in a high boiling solvent at a temperature from 260 to 400° C. batchwise or in a continuous manner and optionally under pressure at $10^5$ to $3.5\times10^7$ Pa or preferably at $10^5$ to $10^7$ Pa. Suitable high boiling solvents are compounds of formula

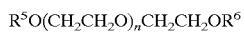

$$R^5O(CH_2CH_2O)_nCH_2CH_2OR^6 \quad \text{III}$$

wherein $R^5$ and $R^6$ each independently signify hydrogen or lower alkyl ($C_1$–$C_4$), and n is 2,3,4,5,6,7 or higher to signify a polyethylenoxy chain.

Examples of solvents of formula III are tetraethylene glycol, tetraethylene glycol dimethyl ether, polyethylene glycol monomethyl ether 350, polyethylene glycol dimethyl ether 400 or polyethylene glycol 350, polyethylene glycol 400, polyethylene glycol 550 and polyethylene glycol 725.

Further suitable high boiling solvents are solvents of formula

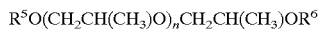

$$R^5O(CH_2CH(CH_3)O)_nCH_2CH(CH_3)OR^6 \quad \text{IV}$$

wherein $R^5$ and $R^6$ are as mentioned above, and wherein n is as mentioned above to signify a polypropylenoxy chain.

A preferred solvent of formula IV is polypropylene glycol 725.

A further preferred solvent is polyoxyethylen-sorbitan-monooleat. The reaction can also be carried out in inorganic salt melts.

In another preferred aspect of the invention the racemization of the compounds of the formula I is carried out in a low boiling organic solvent under pressure at $10^5$ to $3.5\times10^7$ Pa, preferably at $10^5$ to $10^7$ Pa. Suitable solvents are aromatic solvents like benzene, toluene, xylene, or alcohols like methanol, ethanol, propanol, butanol, or a mixture of the mentioned solvents. Preferred solvents are toluene, ethanol or a mixture of both solvents.

According to the invention the racemization is carried out batchwise i.e. by a reaction in which the reactant is added to a reaction system (e.g. round flask) once and after the reaction the product is separated. In the alternative, according to the invention, the racemization is carried out in a continuous manner i.e. by a continuous running reaction in which the reactant is continuously added to a reaction system (e.g. reactor) and the product is continuously separated.

In a further preferred embodiment, the racemization is carried out in the melt at a temperature from 260 to 400° C. under normal or elevated pressure at $10^5$ to $3\times10^5$ Pa or in a preferred way at a temperature from 280 to 380° C. and the same pressure.

In a preferred embodiment a specific amount of the optical active or non-racemic mixture of the intermediate of formula I is heated in a high or low boiling solvent or in the melt form under argon or under nitrogen. The heating is carried out in a device which allows for heating up to 400° C. For small scale the heating can be carried out e.g. with a heating/stirring mantel, an aluminum heating block, an electrically heated reactor or autoclave and the like or by microwave irradiation. For larger scale the heating can be carried out e.g. in reactors or autoclaves. When a low boiling solvent is used the compound of formula I is heated in an autoclave under elevated pressure at $10^5$ to $3.5\times10^7$ Pa. The reaction is carried out batchwise or in a continuous manner. After the reaction, a racemic resolution is carried out and then the (R) or (S) form of the bis(phosphine oxide) of formula I is reduced to the (R) or (S) form of bisphosphine ligands of formula II. Or in an alternative, after the racemization, a reduction of the racemic mixture of compound of formula I to ligands of formula II is carried out and then a racemic resolution is carried out to the (R) or (S) form of the bisphosphine ligands of formula II.

The invention is further concerned with the use of the inventive process for the preparation of atropisomeric ligands of the formula II in the pure (R) or (S) form

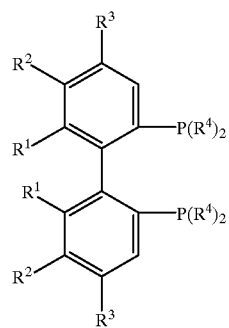

II wherein the symbols are defined as above, characterized in that a) the racemic mixture of bis(phosphine oxides) of formula I is resolved and
b) the (R) or (S) form of the bis(phosphine oxide) of formula I is reduced to the (R) or (S) form of the bisphosphine ligand of formula II or
a) the racemic mixture of bis(phosphine oxides) of formula I is reduced to form a racemic mixture of bisphosphine ligands of formula II and
b) a racemic resolution of the racemic mixture of ligands of formula II is carried out to obtain the (R) or (S) form of the bisphosphine ligand of formula II.

The preparation of compounds of formula I is known and described for example in U.S. Pat. No. 5,274,125.

Both, the racemic resolution and the reduction of compounds of formula I to compounds of formula II are known and described for example in Helvetica Chimica Acta Vol. 74 (1991) p.370 et seq.

In a typical reaction, the thermal racemization is carried out with a compound of formula I in which $R^1$ signifies methoxy, $R^2$ and $R^3$ signify hydrogen, and $R^4$ signifies phenyl ((R) or (S)-MeOBIPHEPO) in a high boiling solvent or in the melt at a temperature from 260 to 400° C. under normal or elevated pressure at $10^5$ to $3.5\times10^7$ Pa or in a low boiling organic solvent at the same temperature under elevated pressure at $10^5$ to $3.5\times10^7$ Pa.

Compounds of formula I are valuable intermediates in the production of biphosphine ligands of formula II, which are used for the formation of complexes with transition metals, especially with transition metals of Group VIII, such as, for example, ruthenium, rhodium or iridium. These complexes are useful as catalysts in asymmetric reactions such as asymmetric hydrogenations. Complexes of diphosphine ligands with transition metals as well as their use for asymmetric reactions such as asymmetric hydrogenations are known and are described, for example, in U.S. Pat. No. 5,430,191.

The following examples illustrate the invention and in no manner represent a limitation thereof. In these examples the abbreviations used have the following significances:

| | |
|---|---|
| HPLC | high performance liquid chromatography |
| NMR | nuclear magnetic resonance spectroscopy |
| rt | room temperature |
| HV | high vacuum |
| e.e. | enantiomeric excess |
| TLC | thin layer chromatography |
| min | minute(s) |
| hr | hour(s) |
| MeOBIPHEPO | (6,6'-dimethoxybiphenyl-2,2'-diyl)bis(diphenylphosphine oxide) |
| DiMeOBIPHEPO | (5,5',6,6'-tetramethoxybiphenyl-2,2'-diyl)bis(diphenylphosphine oxide) |
| pTol-MeOBIPHEPO | (6,6'-dimethoxybiphenyl-2,2'-diyl)bis(di-p-tolylphosphine oxide) |
| PEG 400 | polyethylene glycol 400 |
| Tween 80 | polyoxyethylen-sorbitan-monooleat |

All temperatures are given in degrees Celsius.

EXAMPLE 1

Racemization of (S)-MeOBIPHEPO in polyethylene glycol.

1.1) A 100 ml 2-neck round bottom flask equipped with stirring bar and distillation bridge was charged under argon with 10.0 g (16.28 mmol) of (S)-MeOBIPHEPO [99.2% ee; HPLC-purity: 99.6%] and 50 ml of polyethylene glycol. The mixture was heated for 2 hr. The internal reaction temperature rose from rt to 317° C. within 1 hr. The resulting solution was further stirred for 1 hr whereby the temperature rose to 344° C. and ca. 5 ml of a yellow liquid was collected by distillation. The reaction mixture was cooled to rt, 100 ml of dichloromethane were added and the solution was washed with water (3×40 ml). The organic phase was dried over $MgSO_4$, filtered and the filtrate concentrated to ca. 50 ml. Then, 50 ml of methanol was added and the mixture was concentrated to a volume of ca. 30 ml. This procedure was repeated two more times. The resulting suspension was kept overnight in the refrigerator, the crystals were filtered, washed with cold methanol (2×10 ml) and dried to afford 9.64 g of (RS)-(MeOBIPHEPO) as an off-white solid, HPLC-purity: 96.4%; m.p. 310–312° C. According to an HPLC-analysis on a chiral column (chiral HPLC) this material consisted of a mixture of 50.4% (S)-(MeOBIPHEPO) and 49.6% (R)-(MeOBIPHEPO). $[\alpha]^{20}D=-0.09(c=1.12, CHCl_3)$.

In an analogous experiment, 10 g of (S)-(MeOBIPHEPO) was treated at a maximum temperature of 337° C. for 2.5 hr to afford 9.56 g of (RS)-(MeOBIPHEPO); HPLC-purity: 95.6%; chiral HPLC: 50.5% (S)-(MeOBIPHEPO) and 49.5% (R)-(MeOBIPHEPO).

EXAMPLE 1.2–1.8

In the following examples (S)-MeOBIPHEPO was racemized in the following high boiling solvents: tetraethylene glycol, tetraethylene glycol dimethyl ether, polyethylene glycols 350, 400 and 550, respectively, polypropylene glycol 725 and Tween 80. The results are compiled in Table 1. In all examples a suspension of 150 mg (0.24 mmol) of (S)-MeOBIPHEPO in 2.0 ml of the solvent was heated in a glass tube in an aluminum heating block at 330° C. for 70 min or 350° C. for 40 min. After cooling to rt, the reaction mixture was worked-up and analyzed by HPLC.

TABLE 1

Racemization of (S)-MeOBIPHEPO in different solvents

| example | solvent | T [° C.] | t [min] | work-up[a] | HPLC[b] % (S) | % (R) |
|---|---|---|---|---|---|---|
| 1.2 | tetraethylene glycol | 350 | 40 | 1 | 61 | 39 |
| 1.3 | tetraethylene glycol dimethyl ether | 350 | 40 | 2 | 72 | 28 |
| 1.4 | polyethylene glycol monomethyl ether 350 | 350 | 40 | 3 | 65 | 35 |
| 1.5 | polyethylene glycol dimethyl ether 400 | 350 | 40 | 3 | 60 | 40 |
| 1.6 | polyethylene glycol 550 | 330 | 70 | 1 | 56 | 44 |
| 1.7 | polypropylene glycol 725 | 330 | 70 | 1 | 53 | 47 |
| 1.8 | Tween 80 | 330 | 70 | 1 | 54 | 46 |

[a]Procedure 1: Dissolved in $CH_2Cl_2$, washed with $H_2O$, dried over $Na_2SO_4$, filtered and evaporated.
Procedure 2: Precipitated by addition of hexane and then collected by filtration.
Procedure 3: Precipitated by addition of hexane/toluene. The precipitate was collected by filtration, washed with 3 portions of hexane and dried.
[b]HPLC-analysis on a chiral column.

EXAMPLE 2

Continuous racemization of (R)-MeOBIPHEPO in ethanol.

100 g of (R)-MeOBIPHEPO was dissolved under argon in 1500 ml of ethanol and pumped through a preheater at 200° C. and then through a heated pipe reactor at 350° C. The residence time in the pipe reactor was 15.6 min at a flow rate of 8 ml/min, the pressure increased to $3\times10^6$ Pa. The reaction solution was cooled to rt. Filtration of the crystalline precipitate afforded 63.21 g of a white powder; HPLC-purity 94.7% (RS)-MeOBIPHEPO; chiral HPLC 50:50 mixture of (R)-MeOBIPHEPO and (S)-MeOBIPHEPO; calculated yield 60%. From the mother liquor an additional of 29.75 g of solid material was isolated; HPLC-purity 60.4% (RS)-MeOBIPHEPO; chiral HPLC 50:50 mixture of (R)-MeOBIPHEPO and (S)-MeOBIPHEPO; calculated yield 18%; total yield 78%.

In an analogous experiment the reaction was accomplished with a residence time in the pipe reactor of 10.2 min at a flow rate of 12.2 ml/min. The result was the same as described above.

EXAMPLE 3

Batch racemization of (R)-MeOBIPHEPO in ethanol.

3.1) An autoclave was charged with 1.0 g of (R)-MeOBIPHEPO and 12.5 ml of ethanol, closed and flushed with argon. After heating up to 350° C. in a metal bath, the pressure increased to $1.37 \times 10^7$ Pa. After 30 min the reaction was stopped. The brown solution was evaporated under reduced pressure (52° C./$5.1 \times 10^3$ Pa) to afford 1.0 g of a brown residue of (RS)-MeOBIPHEPO; HPLC purity 84%; chiral HPLC 53.5% (R)-MeOBIPHEPO and 46.5% (S)-MeOBIPHEPO.

Further racemizations of (R)-MeOBIPHEPO under pressure were carried out in various solvents as described in example 3.2–3.8. The results are compiled in Table 2.

TABLE 2

Racemization of 1.0 g (R)-MeOBIPHEPO under pressure in different solvents

| example | solvent [ml] | temp [°C.] | p [Pa] ×10$^5$ | time [min] | crude material [g][a] | % (R)[b] | % (S)[b] |
|---|---|---|---|---|---|---|---|
| 3.1 | EtOH [12.5] | 350 | 137 | 35 | 1.00 | 53.5 | 46.5 |
| 3.2 | PEG400 [5.0] | 330 | — | 90 | 2.18 | — | — |
| 3.3 | Tol/EtOH 7:3 [12.5] | 350 | 78 | 35 | 1.00 | 52.9 | 47.1 |
| 3.4 | PEG 400 [5.0] | 350 | 1 | 35 | 2.28 | 52.8 | 47.2 |
| 3.5 | EtOH [12.5] | 350 | 128 | 35 | 1.02 | 50.5 | 49.5 |
| 3.6 | Tol/EtOH 7:3 [12.5] | 350 | 68 | 35 | 0.99 | 51.5 | 48.5 |
| 3.7 | EtOH [12.5] | 350 | 138 | 50 | 0.97 | 49.7 | 50.3 |
| 3.8 | EtOH [12.5] | 350 | 135 | 20 | 0.93 | 53.5 | 46.5 |

[a] Crude material obtained after evaporation or after aqueous work-up (examples 3.2 and 3.4), respectively.
[b] By HPLC-analysis on a chiral column.

EXAMPLE 4

Racemization of (S)-MeOBIPHEPO in the melt.

4.1) Ten test tubes were charged with 1.0 g each of (S)-MeOBIPHEPO, for a total of 10.0 g (16.3 mmol). The test tubes were heated in the aluminum block at 350° C. for 20 min. After cooling, the oily, brown content of the test tubes was transferred into a round bottom flask using ca. 200 ml of methylene chloride and 200 ml of methanol. The solution was concentrated to a volume of ca. 50 ml and 200 ml of methanol was added. After concentration to ca. 50 ml, the resulting suspension was kept overnight in the refrigerator. The crystals were collected by filtration, washed with cold methanol and dried to afford 8.9 g of (RS)-MeOBIPHEPO as off-white powder; HPLC purity 97%; chiral HPLC 51% (S)-MeOBIPHEPO and 49% (R)-MeOBIPHEPO; calculated yield: 86%.

4.2) An autoclave with stirring bar was charged with 50.0 g of (R)-MeOBIPHEPO, closed and flushed with argon. The reaction was heated to 350° C. The heating was stopped after 45 min. After cooling to rt, the light yellow solid compound obtained was dissolved in 150 ml of $CH_2Cl_2$, the solution transferred into a round bottom flask and evaporated under reduced pressure (50° C./$4 \times 10^3$ Pa). The solid residue was dissolved in 150 ml of MeOH (70° C., reflux) and crystallized in the refrigerator at 4° C. overnight. The crystals were collected by filtration, washed with cold methanol (50 ml) and dried (70° C./$6.5 \times 10^3$ Pa) to afford 42.56 g (yield: 85.1%) of (RS)-MeOBIPHEPO as off-white powder; chiral HPLC 49.9% (S)-MeOBIPHEPO and 50.1% (R)-MeOBIPHEPO.

EXAMPLES 5–8

TABLE 3

Racemization of MeOBIPHEPO analogues were carried out in the melt or in tetraethylene glycol as solvent.

| example | analogue | conc.[a] % | reaction °C. | min | HPLC[b] % (S) | % (R) | remarks |
|---|---|---|---|---|---|---|---|
| 5 | (S)-DiMeOBIPHEPO | 2.2 | 330 | 40 | 70.2 | 29.8 | c) |
| 6 | (R)-DiMeOBIPHEPO | 2.1 | 330 | 240 | 50.3 | 49.7 | c) |
| 7 | (S)-pTol-MeOBIPHEPO | 7.5 | 330 | 60 | 59.7 | 40.3 | c) |
| 8 | (S)-pTol-MeOBIPHEPO | melt | 330 | 60 | 76.5 | 23.5 | d,e) |

[a] Concentration of the MeOBIPHEPO analogue in tetraethylene glycol.
[b] HPLC analysis on a chiral column.
c) Experimental procedure as described in example 1.
d) Experimental procedure as described in example 4.
e) Some decomposition according to TLC analysis.

EXAMPLE 9

Racemization of (S)-MeOBIPHEPO in an organic solvent under microwave irradiation A reactor tube of 40×260 mm fitted with a mechanical stirrer, a reflux condenser and an argon inlet tube was charged with 10.0 g (16.3 mmol) of (S)-MeOBIPHEPO and 50 ml of polyethylene glycol 400. The reactor tube was placed in a microwave reactor. The suspension was stirred under microwave irradiation. The internal reaction temperature rose from rt to 280° C. within 6 min. This temperature was maintained for an additional 64 min. The reactor tube was then removed and allowed to cool. The resulting brown-black solution was analyzed by HPLC on a chiral column and found to contain 52.4% of (S)-MeOBIPHEPO and 46.6% of (R)-MeOBIPHEPO. Work-up and crystallization from methanol afforded 8.9 g (89%) of (RS)-MeOBIPHEPO as an off-white solid; chiral HPLC 50.4% (S)-MeOBIPHEPO and 49.6% (R)-MeOBIPHEPO.

Upon reading the present specification, various alternative embodiments will become obvious to the skilled artisan. These variations are to be considered within the scope and spirit of the invention, which is only limited by the claims that follow and their equivalents.

What is claimed is:

1. A process for the racemization of a compound of the formula I:

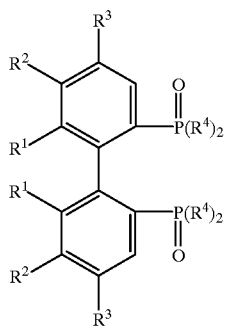

which is present in the (R) form, the (S) form, or a non-racemic mixture of the (R) form and (S) form, wherein $R^1$ is $C_{1-8}$-alkoxy, and $R^2$ is hydrogen, $C_{1-8}$-alkyl, or $C^{1-8}$-alkoxy, or $R^1$ and $R^2$ taken together are methylenedioxy or ethylenedioxy;

$R^3$ is hydrogen, $C_{1-8}$-alkyl, or $C_{1-8}$-alkoxy; and $R^4$ is phenyl or phenyl monosubstituted in the meta- or para-position by, $C_{1-8}$-alkyl, $C^{1-8}$-alkoxy, di- $C_{1-8}$-alkylamino, trialkylsilyl or phenyl;

which comprises heating the compound of formula I to a temperature of from about 260° C. to about 400° C. for a time sufficient to cause racemization of the compound of formula I.

2. The process according to claim 1 wherein the racemization is carried out in a solvent or in a melt.

3. The process according to claim 2 wherein the heating is by microwave irradiation.

4. The process according to claim 2 wherein the heating is in a solvent that has a boiling point above the heating temperature.

5. The process according to claim 4 wherein the heating is in a solvent of formula:

$R^5O(CH_2CH_2O)_nCH_2CH_2OR^6$   III wherein $R^5$ and $R^6$, each independently, are hydrogen or $C_1$–$C_4$-alkyl, and n is an integer greater than 2.

6. The process according to claim 5 wherein n is an integer of from 2 to 7.

7. The process according to claim 4 wherein heating is in a solvent of formula:

$R^5O(CH_2CH(CH_3)O)_nCH_2CH(CH_3)OR^6$   IV wherein $R^5$ and $R^6$, each independently, are hydrogen or $C_1$–$C_4$-alkyl, and n is an integer greater than 2.

8. The process according to claim 7 wherein n is an integer of from 2 to 7.

9. The process according to claim 2 wherein heating is in a solvent selected from the group consisting of tetraethylene glycol, tetraethylene glycol dimethyl ether, polyethylene glycol monomethyl ether 350, polyethylene glycol dimethyl ether 400, polyethylene glycol 350, polyethylene glycol 400, polyethylene glycol 550, polyethylene glycol 725, polypropylene glycol 725, and polyoxyethylen-sorbitan-monooleat.

10. The process according to claim 2 wherein the heating is in a solvent and under a pressure of from about $10^5$ Pa to about $3.5 \times 10^7$ Pa, the solvent having a boiling point above the heating temperature at the pressure used.

11. The process according to claim 10 wherein the heating is in a solvent under a pressure of from about $10^5$ Pa to about $10^7$ Pa.

12. The process according to claim 10 wherein the solvent is an aromatic solvent, an alcohol, or a mixture of an aromatic solvent and an alcohol.

13. The process according to claim 1 wherein the heating is at a temperature of from about 280° C. to about 380° C.

14. The process according to claim 1 wherein the compound of formula I is (6,6'-dimethoxybiphenyl-2,2'-diyl)bis (diphenylphosphine oxide).

15. The process according to claim 1, wherein the compound of formula I is (5,5',6,6'-tetramethoxybiphenyl-2,2'-diyl)bis(diphenylphosphine oxide).

16. The process according to claim 1 wherein the compound of formula I is (6,6'-dimethoxybiphenyl -2,2'-diyl)bis (di-p-tolylphosphine oxide).

* * * * *